United States Patent [19]

Goudie et al.

[11] 4,083,951

[45] Apr. 11, 1978

[54] PHARMACEUTICAL COMPOSITION

[75] Inventors: Alexander Crossan Goudie, Harlow; Harry Seager, Pulborough; Howard Fisher, Worthing, all of England

[73] Assignee: Beecham Group Limited, Great Britain

[21] Appl. No.: 792,118

[22] Filed: Apr. 29, 1977

[30] Foreign Application Priority Data

May 5, 1976 United Kingdom ............... 18329/76

[51] Int. Cl.$^2$ .......................... A61K 31/60; A61L 9/04
[52] U.S. Cl. ....................................... 424/44; 424/230
[58] Field of Search ................................... 424/230, 44

[56] References Cited

U.S. PATENT DOCUMENTS 2,601,285  6/1952  Henderson ........................... 424/230

Primary Examiner—Stanley J. Friedman
Attorney, Agent, or Firm—Jacobs & Jacobs

[57] ABSTRACT

Pharmaceutical compositions containing acetyl salicylic acid or a salt thereof and a ferrous salt having 1 to 7 equivalents of acetyl salicylic acid per equivalent of ferrous ion and characterized by reduced gastric irritation without major reduction of the usual properties of the acetyl salicylic acid. The compositions are orally administrable and may be formulated in one part or in multi-parts with the parts physically separated to prevent premature reaction particularly when the composition is effervescent.

27 Claims, No Drawings

PHARMACEUTICAL COMPOSITION

The present invention relates to pharmaceutical compositions containing acetyl salicylic acid or a salt thereof and a ferrous salt.

Acetyl salicylic acid and its salts are well known anti-inflammatory, analgesic and anti-pyretic agents. Unfortunately acetyl salicylic acid and its salts tend to irritate the stomach linings. Ferrous salts, which are used in treating iron deficiency, have also been reported to disturb the gastro intestinal tract. It has now been discovered that when acetyl salicylic acid or a salt thereof is co-formulated with a ferrous salt then the resulting orally administrable composition has the surprising property of having a reduced propensity to cause gastric irritancy. This effect is not accompanied by any major reduction in the anti-inflammatory, analgesic or anti-pyretic properties of the aspirin.

The reduction in irritant effects can occur in compositions containing quite low levels of ferrous ions, for example, those containing not more than about 7 equivalents of acetyl salicylate per equivalent of ferrous ion present. The improvements are more readily demonstrated in those compositions containing not more than four equivalents of acetyl salicylate per equivalent of ferrous ion and yet more readily demonstrated for those compositions containing not more than 3 equivalents of acetyl salicylate per equivalent of ferrous ion present. We have also found that the compositions of this invention should not contain more than 1 equivalent of ferrous ion per equivalent of acetyl salicylate.

Accordingly, the present invention provides an orally administrable pharmaceutical composition which contains acetyl salicylic acid or a salt thereof and a ferrous salt which composition contains from 1 to 7 equivalents of acetyl salicylic per equivalent of ferrous ion.

Naturally all salts and other components of the compositions of this invention will be pharmaceutically acceptable.

More suitably the compositions of this invention will contain not more than 4, of example not more than 3, equivalents of acetyl salicylate per equivalent of ferrous ion.

Most suitably the compositions of this invention will contain not less than about 2 equivalents of acetyl salicylate thereof per equivalent of ferrous ion, for example they may contain 2 - 4 equivalents of acetylsalicylate per equivalent of ferrous ion.

Some reduction in gastric irritancy occurs when the quantities of acetyl salicylate and ferrous ion are present over the ranges stated but the greatest reduction in gastric irritancy occurs as the ratio between the two components approaches 2 to 1 so that the ratio of components approximates to that which notionally occurs in ferrous acetyl salicylate.

The compositions of this invention may contain acetyl salicylic acid or any of its pharmaceutically acceptable salts such as its sodium, potassium, calcium, magnesium or aluminum salts or mixtures thereof. In general it is preferred to use acetyl salicylic acid or its sodium or calcium salts, particularly acetyl salicylic acid or its calcium salt.

Suitable ferrous salts for inclusion in the compositions of this invention include ferrous sulphate, ferrous gluconate, ferrous citrate, ferrous fumarate, ferrous lactate, ferrous carbonate or mixtures thereof. In general it is preferred to use ferrous sulphate, for example as dried ferrous sulphate or as ferrous sulphate heptahydrate in the compositions of this invention.

It is generally preferable to formulate the present compositions in the form of a unit-dose which contain 100–2000mg of acetyl salicylic acid or a salt thereof and more usually from 300–1000mg of acetyl salicylic acid or a salt thereof.

Out new compositions can benefit from the inclusion of a magnesium salt. Suitably the compositions of this invention contain 1 to 10 and more suitably 2 to 6 equivalents of magnesium ions per equivalent of ferrous ions. Suitable magnesium salts include magnesium carbonate, magnesium oxide, magnesium hydroxide, magnesium sulphate, magnesium citrate, magnesium phosphate and the like.

The stability of the compositions of this invention is generally improved if formulation is effected in such a manner that the acetyl salicylic acid or its salt is separated from the ferrous salt, that is, these components should not be in intimate contact. This may be conveniently achieved by including the acetyl salicylic acid or its salt in a first part of a two-part composition such as a two-part tablet or two-part sachet or the like and including the ferrous salt in a second part of the two part composition. It can be beneficial to separate the first part of the composition from the second part by a physical barrier, for example the dividing partition of the two part sachet or an inert layer separating the two parts of a two part tablet.

When used herein the term "two-part" means "containing at least two parts" so that, for example, three part compositions are included.

In order to obtain their greatest benefit, the compositions of this invention should be dissolved in water prior to ingestion so that the preferred compositions of this invention are those which are readily water soluble.

A particularly convenient method of ensuring that the present compositions are readily dissoluble is to include an effervescent combination within the composition. Effervescent combinations suitable for use include combinations of an alkali metal or alkaline earth metal carbonate or bicarbonate with a solid pharmaceutically acceptable organic acid.

Suitable carbonates and bicarbonates for use include sodium carbonate, sodium bicarbonate, sodium glycine carbonate, and calcium carbonate. Sodium bicarbonate is preferred.

Suitable pharmaceutically acceptable organic acids include hydroxylated di- and tri- carboxylic acids such as citric or tartaric acid and the like. A favoured pharmaceutically acceptable organic acid is citric acid.

Particularly suitable effervescent compositions of this invention will comprise a two-part composition as described hereinbefore in which the part which contains acetyl salicylic acid or its salt also includes an alkali or alkaline earth metal carbonate or bicarbonate and the part which contains the ferrous salt also contains citric acid.

Most suitably the alkali or alkaline earth metal carbonate employed is sodium bicarbonate. Sodium glycine carbonate is also a particularly suitable agent to employ.

Preferred effervescent pharmaceutical compositions according to this invention are two-part unit dose compositions which dissolve in water with the evolution of carbon dioxide, one part of which contains 300mg – 2000mg of acetyl salicylic acid or a salt thereof and an alkali metal or alkaline earth metal carbonate or bicarbonate and the other part of which contains ferrous sulphate and citric acid or tartaric acid and which composition contains approximately 2–7 equivalents of acetyl salicylate per equivalent of ferrous ion.

More suitably these compositions contain 2 – 4 equivalents of acetyl salicylate per equivalent of ferrous ion and preferably about 2 equivalents of acetyl salicylate per equivalent of ferrous ion.

Alternative preferred effervescent pharmaceutical compositions according to this invention are two-part unit dose compositions which dissolve in water with the evolution of carbon dioxide, one part of which contains 300mg – 2000mg of acetyl salicylic acid or a salt thereof and an alkali metal or alkaline earth metal carbonate or bicarbonate and citric acid or tartaric acid and the other part of which contains ferrous sulphate and a disintegrant and which compositions contain approximately 2 – 7 equivalents of acetyl salicylic acid or a salt thereof per equivalent of ferrous ion.

More suitably these compositions contain 2 – 4 equivalents of acetyl salicylate per equivalent of ferrous ion and preferably about 2 equivalents of acetyl salicylate per equivalent of ferrous ion.

Most suitably the preferred effervescent forms of the composition of this invention will contain citric acid.

Most suitably the preferred effervescent forms of the composition of this invention will include sodium bicarbonate or sodium glycine carbonate.

Another particularly convenient method of ensuring that the compositions of this invention are readily dissoluble is to include a dispersant or the like which renders the composition readily dissolvable. Suitable dispersants for use in such compositions include microcrystalline cellulose, starch, cross-linked polyvinylpyrrolidone, sodium carboxymethyl cellulose or other agent known to cause ready dissolution of orally administrable compositions.

Thus preferred dissoluble compositions of this invention are two-part unit-dose compositions one part of which contains 300mg – 2000mg of acetyl salicylic acid or a salt thereof and the other part of which contains ferrous sulphate such that the composition contains approximately 2 – 7 equivalents of acetyl salicylic acid per equivalent of ferrous ion, said composition also comprising dispersant.

The dispersant may be present in either or both parts of the composition. Frequently from 2 – 25% of such dispersants are present in the composition (wt/wt).

More suitably these compositions contain 2 – 4 equivalents of acetyl salicylate per equivalent of ferrous ion and preferably about 2 equivalents of acetyl salicylate per equivalent of ferrous ion.

It is generally preferable that the compositions of this invention contain acetyl salicylic acid or its calcium salt formulated so that the acetyl salicylic acid or its calcium salt is in a dry environment.

It is generally preferable that the compositions of this invention contain ferrous sulphate which is also maintained in a dry environment. This is generally more easily obtained if dried ferrous sulphate is used.

The compositions of this invention may contain conventional excipients used in preparing orally administrable compositions if desired, for example flavouring agents, colouring agents, sweetening agents and the like may be used.

If desired the compositions of this invention may contain an amino acid such as glycine.

The compositions of this invention may be prepared by conventional methods of mixing, tabletting, filling and the like.

The equivalent weight of the acetyl salicylate ion is 179 (this is provided by 180 mg of acetyl salicylic acid, 200 mg of calcium acetyl salicylate). The equivalent weight of ferrous iron is 28 (this is provided by 76 mg of ferrous sulphate dried or 139 mg of ferrous sulphate heptahydrate).

The following Examples illustrate the invention:

EXAMPLE 1

The following ingredients were mixed and filled into one part of a two-part sachet:

| | |
|---|---|
| Acetyl salicylic acid | 500 mg |
| Sodium Bicarbonate | 270 mg |
| Magnesium Oxide | 80 mg |
| Calcium Carbonate | 80 mg |
| Flavours | qs |
| Sweetening Agents | qs |

The following ingredients were mixed and filled into the second part of the two-part sachet:

| | |
|---|---|
| Ferrous Sulphate heptahydrate | 386 mg |
| Citric Acid | 50 mg |
| Flavours | qs |
| Sweetening Agents | qs |

In this formulation the flavours and sweetening agents (e.g. saccharin salts and sugars) are optional.

EXAMPLE 2

A similar effervescent composition to that described in Example 1 was prepared in which the acetyl salicylic acid was replaced by the equivalent weight of its calcium salt.

EXAMPLE 3

The following two-part sachet was prepared:

| Contents of 1st Part | | Contents of 2nd Part | |
|---|---|---|---|
| Acetyl salicylic acid | 1000 mg | Dried Ferrous Sulphate | 275 mg |
| Sodium Bicarbonate | 270 mg | Sucrose | 300 mg |
| Magnesium Oxide | 80 mg | Flavours | qs |
| Calcium Carbonate | 80 mg | Calcium Saccharin | qs |
| Citric Acid | 50 mg | | |
| Flavours | qs | | |
| Calcium Saccharin | qs | | |

EXAMPLE 4

A similar effervescent composition to that described in Example 3 was prepared in which the acetyl salicylic acid content was reduced to 600 mg.

EXAMPLE 5

An effervescent tablet may be prepared which contains an inner core containing ferrous sulphate which is surrounded by an inert layer which is itself surrounded by a layer containing acetyl salicylic acid. The tablet may contain the following ingredients:

| Core | |
|---|---|
| Ferrous Sulphate heptahydrate | 75 mg |
| Polyethyleneglycol 4000 | 15 mg |
| Sodium Bicarbonate | 18.6 mg |
| Anhydrous Lactose | 18.6 mg |
| Tartaric Acid | 22.8 mg |
| Inert Layer | |
| Anhydrous Lactose | 500 mg |
| Polyethyleneglycol 4000 | 50 mg |
| Outer Layer | |
| Acetyl salicylic acid | 300 mg |
| Sodium Bicarbonate | 20 mg |
| Polyethyleneglycol 4000 | 70 mg |
| Tartaric Acid | 244 mg |
| Anhydrous Lactose | 200 mg |

EXAMPLE 6

A tablet as described in Example 5 was prepared in which the ferrous sulphate heptahydrate was replaced by 100 mg of dried ferrous sulphate.

EXAMPLE 7

The following two-part sachet was prepared:

| Contents of 1st Part | | Contents of 2nd Part | |
|---|---|---|---|
| Calcium acetyl salicylate | 300 mg | Dried Ferrous Sulphate | 200 mg |
| Sodium Bicarbonate | 300 mg | Sucrose | 300 mg |
| Citric Acid | 50 mg | Colours | qs |
| Flavours | qs | | |
| Calcium Saccharin | qs | | |
| Colours | qs | | |

EXAMPLE 8

A sachet may be prepared as in Example 7 but replacing the sodium bicarbonate with 900 mg of sodium glycine carbonate.

EXAMPLE 9

Pharmacology
a. Analgesic Effects

Sodium acetyl salicylate and mixtures of sodium acetyl salicylate and ferrous sulphate (2:1 ratio of equivalents) were tested against phenylquinone induced writhing in the mouse. Dose responses were plotted in terms of acetyl salicylate content and the following $ED_{50}$ values obtained:

| Sodium acetyl salicylate | 56 mg/kg |
|---|---|
| Sodium acetyl salicylate + ferrous sulphate | 51 mg/kg | indicating no statistically significant difference in activity between the two compositions.

b. Gastric Irritancy

When tested in starved rats (18 hr. fasted) with a 1 hour contact time the following results were obtained:

| Compound | Dose mg/kg | No. of rats | % incidence gastric erosions |
|---|---|---|---|
| Sodium acetyl salicylate | 338 | 8 | 75 |
| Sodium acetyl salicylate + ferrous sulphate* | 338 + 232 | 8 | 0 |
| Sodium acetyl salicylate + ferrous sulphate** | 338 + 232 | 8 | 25 |
| Sodium acetyl salicylate | 160 | 8 | 88 |
| Sodium acetyl salicylate + ferrous sulphate* | 169 + 116 | 8 | 13 |

-continued

| Compound | Dose mg/kg | No. of rats | % incidence gastric erosions |
|---|---|---|---|
| Sodium acetyl salicylate + ferrous sulphate* | 169 + 58 | 8 | 63 |
| Calcium acetyl salicylate | 100 | 8 | 25 |
| Calcium acetyl salicylate + ferrous sulphate** | 100 + 77 | 8 | 0 |

*Mixture made from dry compounds
**Constituents dosed as solutions

When administered to 5 human volunteers no gastric irritation was reported for a solution of ferrous sulphate (600 mg) with sodium acetyl salicylate (900 mg) whereas gastro intestinal disturbances were reported for a solution of ferrous sulphate (600 mg) alone.

What we claim is:

1. An orally administrable pharmaceutical composition which contains acetyl salicylic acid or a salt thereof and a ferrous salt which composition contains from 1 to 7 equivalents of acetyl salicylate per equivalent of ferrous ion.

2. A composition as claimed in claim 1 containing not more than 4 equivalents of acetyl salicylate per equivalent of ferrous ion.

3. A composition as claimed in claim 1 containing not more than 3 equivalents of acetyl salicylate per equivalent of ferrous ion.

4. A composition as claimed in claim 1 which contains not less than 2 equivalents of acetyl salicylate per equivalent of ferrous ion.

5. An orally administrable pharmaceutical composition which contains acetyl salicylic acid or a salt thereof and a ferrous salt which composition contains 2 equivalents of acetyl salicylate per equivalent of ferrous ion.

6. A composition as claimed in claim 1 which contains acetyl salicylic acid or its calcium salt.

7. A composition as claimed in claim 1 which contains ferrous sulphate.

8. A composition as claimed in claim 1 which contains a magnesium salt which provides 1 to 10 equivalents of magnesium ion per equivalent of ferrous ion present.

9. A composition as claimed in claim 8 which contains 2 to 6 equivalents of magnesium ion per equivalent of ferrous ion.

10. A composition as claimed in claim 1 in which the acetyl salicylic acid or its salt is physically separated from the ferrous salt.

11. A composition as claimed in claim 10 wherein the acetyl salicylic acid or its salt is in the first part of a two-part composition and the ferrous salt is in a second part of that two-part composition.

12. A composition as claimed in claim 11 in the form of a two-part tablet or a two-part sachet.

13. A composition as claimed in claim 1 which also comprises an effervescent combination.

14. A composition as claimed in claim 13 wherein the effervescent combination comprises an alkali or alkaline earth metal carbonate or bicarbonate and a solid organic acid.

15. A composition as claimed in claim 14 wherein the organic acid is citric acid.

16. A composition as claimed in claim 13 which contains sodium bicarbonate.

17. A composition as claimed in claim 13 which contains sodium glycine carbonate.

18. A composition as claimed in claim 11 in the form of a two-part unit-dose composition which dissolves in water with the evolution of carbon dioxide, one part of which contains 300mg – 2000mg of acetyl salicylic acid or a salt thereof and an alkali metal or alkaline earth metal carbonate or bicarbonate and the other part of which contains ferrous sulphate and citric acid or tartaric acid and which composition contains approximately 2 – 7 equivalents of acetyl salicylate per equivalent of ferrous ion.

19. A composition as claimed in claim 11 in the form of a two-part unit-dose composition which dissolves in water with the evolution of carbon dioxide, one part of which contains 300mg – 2000mg of acetyl salicylic acid or a salt thereof and an alkali metal or alkaline earth metal carbonate or bicarbonate and citric acid or tartaric acid and the other part of which contains ferrous sulphate and a disintegrant and which composition contains approximately 2 – 7 equivalents of acetyl salicylic acid or a salt thereof per equivalent of ferrous ion.

20. A composition as claimed in claim 18 which contains 2 equivalents of acetyl salicylate per equivalent of ferrous ion.

21. A composition as claimed in claim 18 which contains citric acid.

22. A composition as claimed in claim 18 which contains sodium bicarbonate.

23. A composition as claimed in claim 18 which contains sodium glycine carbonate.

24. A dissoluble composition composed as in claim 11 in the form of a two-part unit-dose composition one part of which contains 300mg – 2000mg of acetyl salicylic acid or a salt thereof and the other part of which contains ferrous sulphate such that the composition contains approximately 2 – 7 equivalents of acetyl salicylic acid per equivalent of ferrous ion, said composition also comprising 2 – 25% by weight of dispersant.

25. A composition as claimed in claim 1 which contains dried ferrous sulphate.

26. A composition as claimed in claim 1 which contains acetyl salicylic acid.

27. A composition as claimed in claim 1 which contains calcium acetyl salicylate.

* * * * *